United States Patent
Crowley et al.

(10) Patent No.: US 11,794,034 B1
(45) Date of Patent: Oct. 24, 2023

(54) INFUSION DEVICES AND METHODS OF USING THEM

(71) Applicants: James Crowley, Roanoke, VA (US); Jackson Kiser, Roanoke, VA (US); Sean O Wilson, Roanoke, VA (US)

(72) Inventors: James Crowley, Roanoke, VA (US); Jackson Kiser, Roanoke, VA (US); Sean O Wilson, Roanoke, VA (US)

(73) Assignee: Carilion Clinic, Roanoke, VA (US)

( * ) Notice: Subject to any disclaimer, the term of this patent is extended or adjusted under 35 U.S.C. 154(b) by 784 days.

(21) Appl. No.: 16/384,660

(22) Filed: Apr. 15, 2019

Related U.S. Application Data

(60) Provisional application No. 62/657,124, filed on Apr. 13, 2018.

(51) Int. Cl.
| | |
|---|---|
| *A61N 5/10* | (2006.01) |
| *A61M 5/14* | (2006.01) |
| *A61M 5/00* | (2006.01) |
| *A61L 31/02* | (2006.01) |
| *A61K 51/04* | (2006.01) |
| *A61L 31/04* | (2006.01) |

(52) U.S. Cl.
CPC ........ *A61N 5/1007* (2013.01); *A61K 51/0482* (2013.01); *A61L 31/022* (2013.01); *A61L 31/048* (2013.01); *A61M 5/002* (2013.01); *A61M 5/1417* (2013.01); *A61N 5/1048* (2013.01); *A61L 2400/12* (2013.01); *A61M 2205/58* (2013.01); *A61N 2005/1021* (2013.01); *A61N 2005/1089* (2013.01); *A61N 2005/1094* (2013.01)

(58) Field of Classification Search
CPC .... A61N 2005/1021; A61N 2005/1094; A61N 2005/1085–1098; A61N 5/10–1084; A61M 5/002; A61M 5/007; A61M 5/14; A61M 5/1417
See application file for complete search history.

(56) References Cited

U.S. PATENT DOCUMENTS

| | | | |
|---|---|---|---|
| 6,217,503 B1 * | 4/2001 | Weinberger | A61N 5/1002 600/7 |
| 2011/0124948 A1 * | 5/2011 | Yokell | A61M 5/1407 600/5 |
| 2011/0178359 A1 * | 7/2011 | Hirschman | G21G 4/08 600/4 |
| 2012/0305800 A1 * | 12/2012 | Mayfield | G21G 1/0005 250/506.1 |
| 2014/0296611 A1 * | 10/2014 | Schwartz | A61N 5/1007 600/7 |
| 2015/0327941 A1 * | 11/2015 | Haynes | A61B 90/02 600/3 |
| 2018/0345037 A1 * | 12/2018 | Starz | A61M 5/1417 |

* cited by examiner

*Primary Examiner* — Thaddeus B Cox
(74) *Attorney, Agent, or Firm* — Rhodes IP PLC; Christopher R. Rhodes

(57) ABSTRACT

Certain configurations of an infusion device are described. In some examples, the infusion device may comprise an enclosure that can absorb radiation from a radioisotope material within the enclosure. The enclosure can also be configured to permit administration of the radioisotope material within the enclosure to a human in need of treatment for a condition such as cancer.

21 Claims, 7 Drawing Sheets

INFUSION DEVICES AND METHODS OF USING THEM

PRIORITY APPLICATION

This application is related to and claims priority to U.S. Provisional Application No. 62/657,124 filed on Apr. 13, 2018, the entire disclosure of which is hereby incorporated herein by reference.

BACKGROUND

Administration of radiotherapies can be difficult due to potential exposure of staff to the radiation. Radiotherapy administration requires monitoring of staff exposure to radiation.

SUMMARY

Certain aspects, examples and configurations are directed to infusion devices that can be used to deliver radioisotope therapy to a human in need of treatment. Targeted radioisotope or radionuclide therapy can be used to treat a human for cancer or other conditions.

In an aspect, an infusion device configured to permit infusion of a radioisotope therapy material in a container within the infusion device comprises a base and a lid. In some instances, each of the base and the lid is configured to absorb beta radiation emissions from the radioisotope therapy material and is configured to absorb gamma ray emissions from the radioisotope therapy material. In certain configurations, the base and lid together are sized and arranged to receive the container. In some instances, the base comprises a port to access the radioisotope therapy material in the container without removing the lid from the housing to permit infusion of the radioisotope therapy material in the container to a human subject in need of treatment using the radioisotope therapy material.

In certain embodiments, the lid removably couples to the base through a magnet in the base or through hook and loop fastener or other means. In some examples, the base comprises a first material comprising a polymeric material to absorb the beta radiation emissions and a second material comprising a metal to absorb the gamma ray emissions. In other examples, the polymeric material comprises an acrylic and the metal comprises one or more of lead, antimony, bismuth, and tin. In some examples, the metal is present as metal nanoparticles. In certain embodiments, the infusion device further comprises an electronic device in the base or the lid or both. In some examples, the electronic device comprises an internal radiation sensor, a processor or other devices. In some examples, the container is permanently coupled to the base to prevent removal of the container from the base.

In another aspect, an infusion device comprises an enclosure, and a radioisotope therapy material in the enclosure, wherein the enclosure comprises a port to access the radioisotope therapy material in the enclosure, and wherein the enclosure is configured to absorb beta radiation emissions from the radioisotope therapy material and to absorb gamma ray emissions from the radioisotope therapy material.

In certain embodiments, the enclosure further comprises a lid removably coupled to a base. In some examples, the lid removably couples to the base through hook and loop fastener or through a magnet or other means. In some examples, the enclosure comprises a first material comprising a polymeric material to absorb the beta radiation emissions and a second material comprising a metal to absorb the gamma ray emissions. In some embodiments, the polymeric material comprises an acrylic and the metal comprises one or more of lead, antimony, bismuth, and tin. In certain instances, the metal is present as metal nanoparticles. In some examples, the device may comprise an electronic device in the enclosure, e.g., an internal radiation sensor, a processor, etc. In some embodiments, the radioisotope therapy material is present in a container that is permanently coupled to the enclosure.

In an additional aspect, a process of infusing a radioisotope therapy material to a human subject in need of treatment using the radioisotope therapy material comprises administering a radioisotope therapy material using an infusion device as described herein. In some instances, the infusion device comprising the radioisotope therapy is placed on an intravenous (IV) pole during the process. In other embodiments, the radioisotope therapy material is administered by fluidically coupling the infusion device to a fluid line of the human, e.g., an IV line or artery line, in need of therapy using the radioisotope therapy material. In some embodiments, the radioisotope therapy material is lutetium-177-dotatate. In certain examples, the infusion device comprising the lutetium-177-dotatate is placed on an IV pole during the process.

In another aspect, a process of treating a human in need of treatment for cancer comprises administering a targeted radioisotope therapy material to the human in need of treatment using a an infusion device as described herein. In some examples, the infusion device comprising the radioisotope therapy for treating cancer is placed on an IV pole during the process. In some instances, the radioisotope therapy material for treating cancer is administered by fluidically coupling the infusion device to a fluid line of the human in need of therapy using the radioisotope therapy material. In some embodiments, the radioisotope therapy material is lutetium-177-dotatate to treat a neuroendocrine tumor. In other embodiments, the infusion device comprising the lutetium-177-dotatate is placed on an IV pole during the process.

In another aspect, a kit for treating a human in need of treatment for cancer comprises an infusion device as described herein and a radioisotope therapy material. In some instances, the radioisotope therapy material is lutetium-177-dotatate to treat a neuroendocrine tumor. The kit may further comprise written or electronic instructions for treatment of the human using the infusion device and the lutetium-177-dotatate. In other instances, the radioisotope therapy material is lutetium-177-prostate specific membrane antigen to treat prostate cancer. The kit may further comprise written or electronic instructions for treatment of the human using the infusion device and the lutetium-177-prostate specific membrane antigen.

Additional aspects, embodiments, configurations and examples are described in more detail below.

BRIEF DESCRIPTION OF THE SEVERAL VIEWS OF THE DRAWINGS

Certain aspects, configurations and illustrations are described with reference to the accompanying figures in which.

It will be recognized by the person having ordinary skill in the art, given the benefit of this disclosure, that the dimensions and components in the figures are not necessarily drawn to scale. Different dimensions, shapes and the like may be used as desired.

DETAILED DESCRIPTION

Certain infusion devices and methods of using them are described that can be used to deliver radioisotope therapy to a human in need of treatment while reducing exposure of staff to radiation. In some instances, the infusion device may comprise one or more enclosures which can be designed to absorb radiation emissions during the infusion process. The exact type of material used can depend, at least in part, on the type of radiation emitted by the radioisotope therapy material within the infusion device. In some instances, the enclosure material used in the infusion device can be selected to absorb beta radiation. In other instances, the enclosure material used in the infusion device can be selected to absorb gamma radiation. In additional configurations, the enclosure material or materials used can be selected to absorb both beta and gamma radiation. For example, the infusion device may comprise two or more different enclosure materials with one enclosure material selected to absorb beta radiation and the other enclosure material selected to absorb gamma radiation. If desired, the material can be selected to absorb alpha radiation, Auger electrons or other radiative emissions.

In some configurations, the infusion devices described herein comprise an enclosure which can be used to absorb radiation and may also be sized and arranged to receive one or more containers constructed and arranged to retain a radioisotope therapy material. For example, the enclosure can be sized and arranged to receive a container which can hold a solution of a radioisotope therapy material that can be used to treat a human in need of treatment, e.g., for cancer or other medical conditions. The radioisotope therapy solution may be present in a bag or other container which can be placed within the enclosure to shield the surrounding environment from radiation emitted by the radioisotope therapy material in the container. In some instances, the enclosure may comprise one or more apertures or ports that permit use of the radioisotope therapy material in the enclosure without the need to remove the radioisotope therapy material contained within the enclosure. This configuration dramatically reduces radiation exposure to staff, simplifies administration of the radioisotope therapy material and permits staff to stand, for example, within a few feet of the human being administered the radioisotope therapy material.

Figure 1:
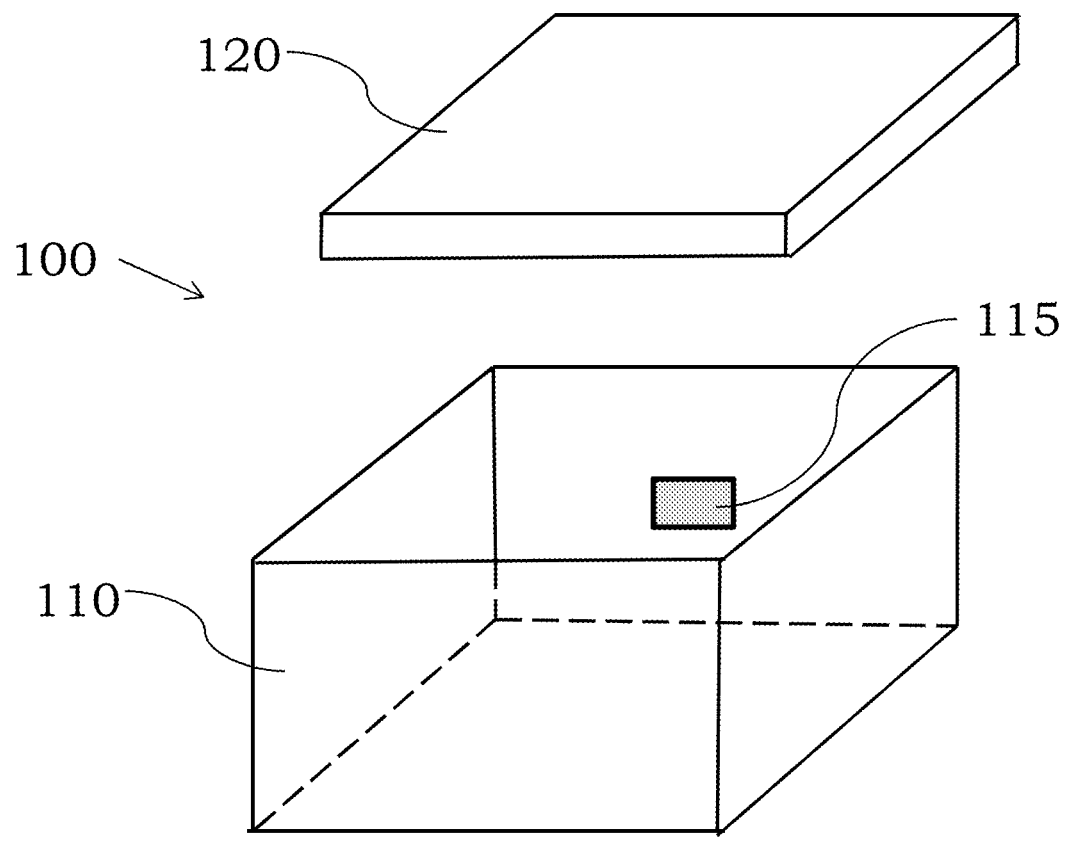
FIG. 1 an illustration of an infusion device comprising a lid and a base, in accordance with some examples.

In certain examples and referring to FIG. 1, an infusion device 100 is shown that comprises a base 110 and a lid 120 which together forming an enclosure. The lid 120 can be removable or fixed. In the case of a fixed lid, the radioisotope therapy material can be added to the infusion device 100 at a production facility, and then the lid 120 can be sealed to the base 110 so the radioisotope therapy material may not be removed except through an interface or fitting which protrudes through the aperture 115. In other instances, the lid 120 can be removable. For example a removable lid can be coupled to the base 110 through numerous different means including hinges, magnets, hook and loop fastener, screws, bolts or other means. The base 110 typically comprises at least one aperture 115 that can be used to access the radioisotope therapy material within the infusion device 100. If desired, a second aperture may also be present to permit introduction and/or removal of a fluid or other material into the container within the infusion device 100. In some instances, the aperture 115 can be used to withdraw or infuse the radioisotope therapy material into a human by way of an intravenous line or other fluid line coupled to a vein or artery of the human in need of treatment. For example, a pump or other means can be coupled to a container housed within the infusion device 100 to withdraw liquid from the container within the infusion device 100, and liquid including radioisotope therapy material may be provided to an IV line coupled to a vein or artery of the human in need of treatment. Alternatively, a selected amount of liquid can be introduced into the container within the infusion device to provide a desired level of radioisotope therapy material per volume of fluid, and the radioisotope therapy material solution can then be provided to the human in need of treatment, e.g., by way of tubing fluidically coupled to an intravenous (IV) line. This process permits infusion of the radioisotope therapy material without the need to do a periodic "push" through the IV line and provides for more consistent delivery of a desired amount of radioisotope therapy material.

In some examples, the base or lid (or both) of the infusion device may comprise one or more materials that can absorb radiation emitted by the radioisotope therapy material to shield staff, the patient and other people from the radiation during the treatment process. In some instances, the radioisotope therapy material can emit radiation by a single radiative process, whereas in other instances the radioisotope therapy material can emit radiation by two or more radiative processes or may emit radiation of two or more different types. For example, the radioisotope therapy material can emit radiation by alpha decay, beta decay or gamma decay. In alpha decay, an alpha particle (helium nucleus) is emitted by the radioisotope therapy material. In beta decay, an electron (or positron) is emitted by the radioisotope therapy material. In gamma decay, a photon, e.g., a gamma ray, is emitted by the radioisotope therapy material. The infusion devices described herein are particularly suitable for absorbing radiation emitted by way of beta decay and gamma decay but can also be used for alpha decay emissions.

In some embodiments, the infusion devices described herein may comprise a polymeric material that can absorb radiation that is emitted by beta decay, gamma decay or both. In some embodiments, the enclosure material may comprise one or more thermoplastic materials or thermosetting materials. For example, suitable materials that can be used in the base and lid of the infusion device include, but are not limited to, an acrylic, an acrylonitrile butadiene styrene, a nylon, a polylactic acid, a polybenzimidazole, a polycarbonate, a polyether sulfone, a polyether ether ketone, a polyetherimide, a polyethylene, a polypropylene, a polyphenylene oxide, a polyphenylene sulfide, a polystyrene, a polyvinyl chloride, a polyvinyledene fluoride, a polytetrafluoroethylene, a polyurethane, a polyester, an epoxy or epoxide material, a polyimide, a maleimide, a bismaleimide, a cyanate ester, a vinyl ester or other materials. In some embodiments, the base or the lid or both may comprise an acrylate, a polyacrylate, a polyolefin, and a co-polymer thereof. In certain embodiments, the base and lid may each comprise a homopolymer of acrylic acid or an acrylic acid that has been cross-linked with an ether or other material. The material of the base and lid is typically rigid to retain a fluid container within the infusion device, though it may be flexible or flexible at least to some degree if desired. In some embodiments, the base, the lid or both may comprise poly (methylmethacrylate) or another form of an acrylic glass. The base or lid or both may be colored, colorless, transparent or opaque as desired. In certain examples, the infusion device may comprise one or more metal materials that can absorb radiation including, but not limited to, lead (Pb), tin (Sn), antimony (Sb), bismuth (Bi), or mixtures of these materials with other metals or non-metals.

In some embodiments, the material used in the infusion device may comprise two or more different materials. For example, lead (Pb) by itself may be ineffective at absorbing beta particles, since beta particles can produce secondary radiation as they pass through elements with a high atomic number. In other embodiments, the infusion device may comprise two different materials with a first material selected to absorb radiation emitted by way of beta decay, and the second material selected to absorb radiation emitted by way of gamma decay. For example, a combination of materials including Pb and a plastic such as a polyacrylate can be used to absorb both beta emissions and gamma emissions. The polymeric materials may be used in combination with metal particles or other particulate materials that can also absorb radiation at least to some degree. For example, lead nanoparticles, nanostructures or nanosystems may be present in combination with the polymeric materials to provide an enclosure which can absorb different types of radiative emissions. Alternatively, a sheet or sections of a polymeric material can be sandwiched between sheets of lead or other metals to provide a composite material comprising the two different materials. In another instances, metal particles, metal fibers or other metal structures can be trapped within a network of the polymeric material to absorb two or more different radiation emissions using the combined materials. These configurations permit use of the infusion device with a wide range of radioisotope therapy materials.

In certain embodiments, the infusion devices described herein can be used with many different types of radioisotope therapy materials. The radioisotope therapy materials can be specific, e.g., to target certain disorders, cells, etc. by binding to one or more receptors or sites on the cells, tissue, etc. or may be systemic, e.g., administered to the whole body and acting on many different cell types. Without wishing to be bound by any one theory or particular material, radioisotope therapy typically works by altering nucleic acid material inside cells to deactivate, kill or otherwise stop the growth of certain cells. The radioisotope therapy may shrink tumors, e.g., in pre-operative therapy or neoadjuvant therapy, may kill cancer cells or kill residual cancer cells (following other treatment) or may prevent recurrence of cancer. Using the infusion devices described herein, the radioisotope therapy is typically administered by brachytherapy through an IV line, artery line or other line that introduces a solution into a human. Additional treatment modalities including chemotherapy, external radiation, surgery and the like can be used in addition to or in combination with the radioisotope therapy methods using the infusion devices described herein.

In some instances, the radioisotope is typically present in a compound designed to provide targeted radionuclide therapy to target specific cells or tissues. Without wishing to be bound by any one configuration, the targeted radionuclide therapy material typically comprises a ligand or binding moiety to target specific cells and a radionuclide moiety to deliver radiation to the targeted cells upon binding of the binding moiety of the targeted radionuclide material to the cell. Binding of the binding moiety to the target cell places the radionuclide in proximity to the cells so radiative emissions are received by the target cells. In some instances, radionuclides that emit alpha particles can emit radiation within a few cell diameters, which can minimize radiation exposure of non-targeted cells.

In certain embodiments, the exact radioisotope or radionuclide used with the infusion devices described herein can vary depending on the particular disorder to be treated. In some embodiments, the radioisotope therapy can be administered in an effective amount to treat a specific disorder or disease. For example, lutetium-177-DOTATATE, lutetium-177-DOTATAC, yttrium-90-DOTATATE, or yttrium-90-DOTATAC can be used to treat neuroendocrine tumors. Strontium-189 chloride, samarium-153, radium-223 and radium-223 dichloride can be used to treat prostate cancer. Yttrium-90 ibritumomab tiuxetan and iodine-131 tositumomab can be used to treat indolent B-cell lymphoma. Yttrium-90 and iodine-131 can be used in tandem with monoclonal antibodies to treat non-Hodgkin's lymphoma. Samarium-153-EDTMP and strontium-89-chloride can be used for palliation of bone metastases. In other instances, a radionuclide material may comprise one or more of bromine-77, indium-111, iodine-123, and iodine-125, lutetium-177, holmium-166, rhenium-186, rhenium-188, copper-67, promethium-149, gold-199, technetium-99m, strontium-89, radium-223, gallium-68, thorium-227, actinium-225 and rhodium-105. Some of these radioisotopes can be used in imaging applications, whereas other radioisotopes, e.g., beta and alpha emitters, are typically used in targeted radionuclide therapy materials. The binding moiety used with the radionuclide may vary and can be based on heme rings, peptides, lipids or other groups that can bind specifically to a receptor on a cell.

In certain examples, additional materials may be administered or co-administered with the radioisotope therapy material. These materials can introduced into the container within the housing or may be infused or mixed separately with the radiotherapy material. Illustrative materials include, but are not limited to, sugars, amino acids, lipids, other pharmaceutical agents such as anti-carcinogenic materials including chemotherapeutic materials, biological or bioactive materials such as monoclonal antibodies, interferon, interleukins or other materials.

Figure 2:
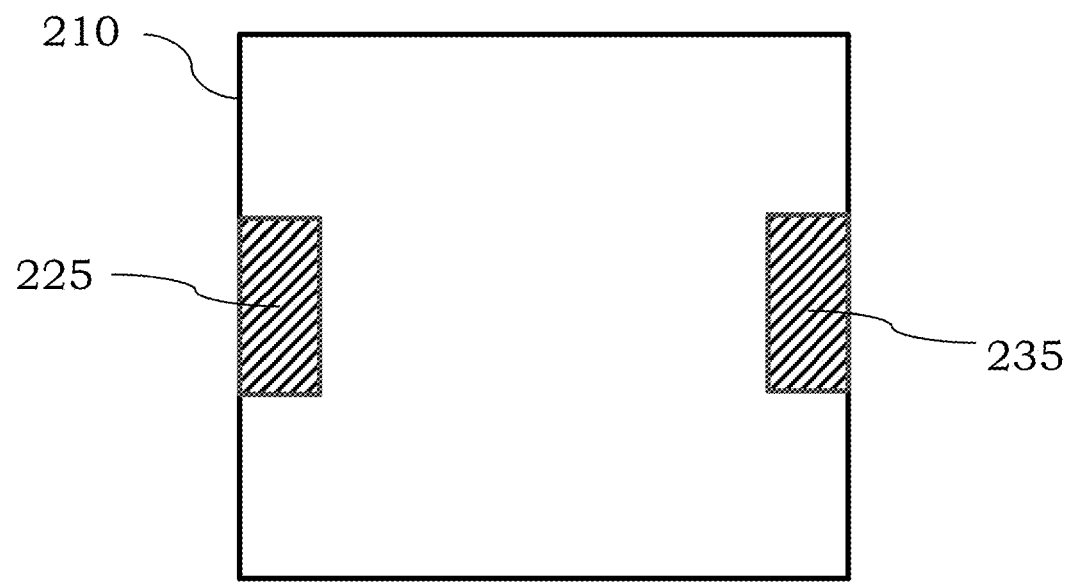
FIG. 2 is top view of a base showing magnets which can be used to couple a lid to the base, in accordance with certain embodiments.
Figure 3:
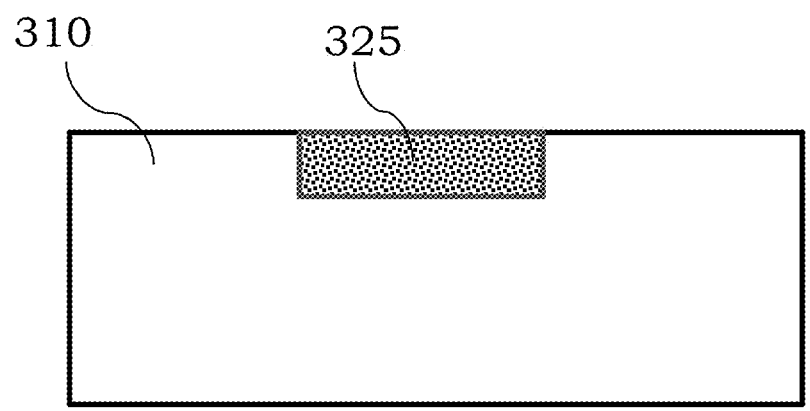
FIG. 3 is side view of a base showing hook and loop fastener on one surface of a base, in accordance with some examples.
Figure 4:
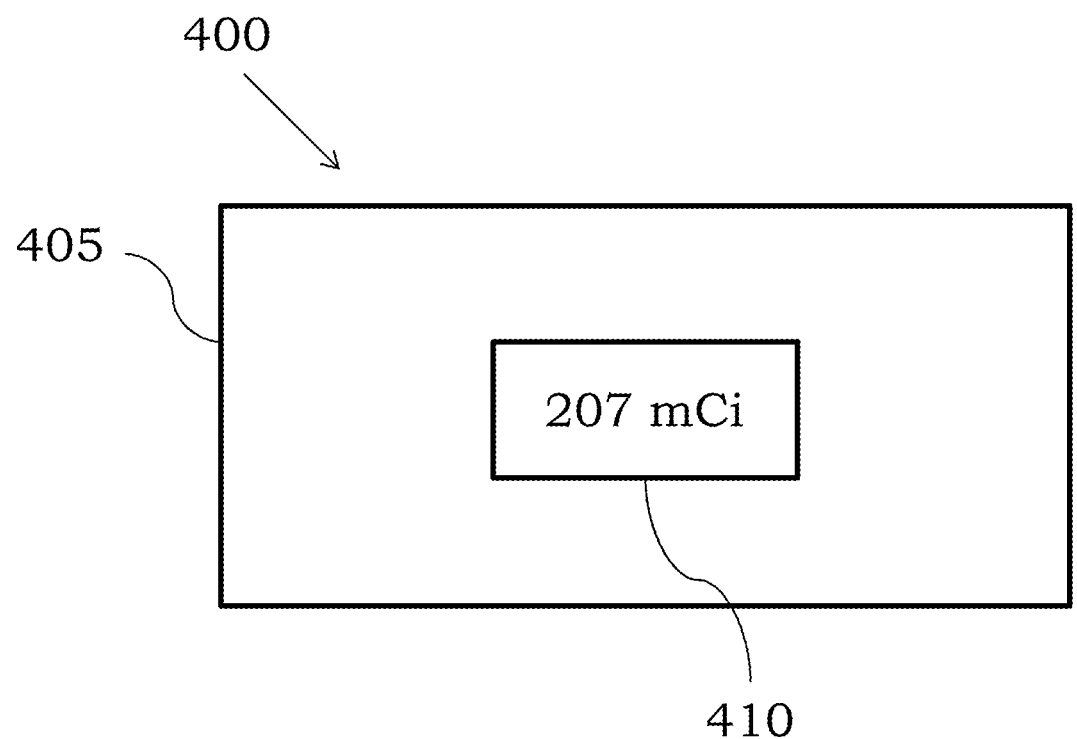
FIG. 4 is an illustration showing a display present on an infusion device, in accordance with certain embodiments.
Figure 5:
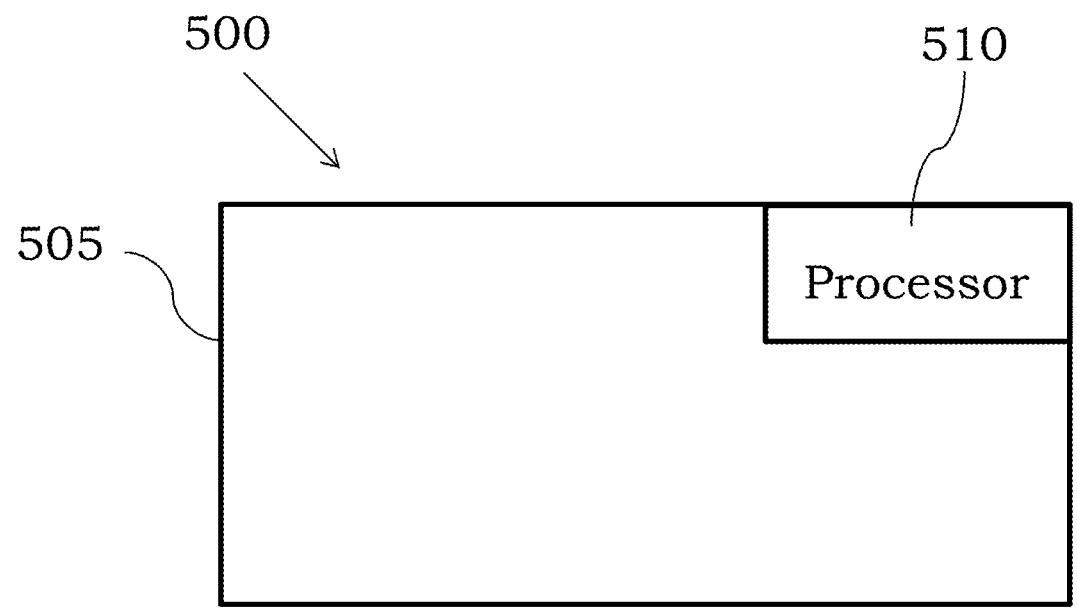
FIG. 5 is an illustration showing a processor present on an infusion device, in accordance with some embodiments.

In certain examples, the infusion devices described herein may comprise one or more electronic devices to facilitate use of the infusion device for radioisotope therapy treatment. For example, the infusion device may comprise an internal radiation sensor, e.g., a photodiode such as, for example, a silicon PIN photodiode, to permit measurement of the amount of radioactivity in the enclosure. The presence of the shielding materials in the enclosure can make it difficult to measure the radioactivity of the radioisotope therapy externally without removing the lid or the removing the material from the enclosure. Where the enclosure is sealed, the internal radiation sensor can be used to provide an indicator of current radioactivity levels prior to administration. A simplified illustration is shown in FIG. 2, where a top view of an infusion device 200 comprising a display 210 that can display a radiation level of material in the enclosure 205 is shown. For example, the display 210 can be electrically coupled to an internal radiation sensor (not shown) which can measure the radioactivity of the radioisotope material in the infusion device to assist in determining a dose calibration prior to administration of the radioisotope material. Depending on the particular radioisotope therapy material used, a selected dosage, e.g., 100-300 milliCuries, can be administered in one or more doses over a desired treatment window, e.g., every 2-8 weeks for 1, 2, 3 4 or more doses and for a treatment period, e.g., over 20 minutes to about 120 minutes. Alternatively, the display may provide electronic instructions to staff regarding the administration steps or processes to be used to treat the human using the radioisotope therapy material.

In other examples, the infusion device may also comprise one or more processors, such as microprocessor, to control the various sensors and devices. The processor may be coupled to a memory unit or have an integral memory unit to be able to store radiation readings, infusion times, etc. In other examples, the infusion device may comprise a flow sensor, a communication chip such as a Bluetooth chip, a radio frequency tag or other electronic components. For example, a mobile device such as a tablet, laptop, phone, etc. can communicate with the infusion device to monitor radioactivity, infusion treatment or other parameters to permit staff to be further away from the source of radiation. The processor is typically a commercially available processor such as the well-known Pentium class processors available from the Intel Corporation. Many other processors are also commercially available. Such a processor usually executes an operating system which may be, for example, the Windows 95, Windows 98, Windows NT, Windows 2000 (Windows ME), Windows XP, Windows Vista, Windows 7, Windows 8 or Windows 10 operating systems available from the Microsoft Corporation, MAC OS X, e.g., Snow Leopard, Lion, Mountain Lion or other versions available from Apple, the Solaris operating system available from Sun Microsystems, or UNIX or Linux operating systems available from various sources. Alternatively, a dedicated operating system written specifically for the infusion device could also be used.

In certain examples, the infusion devices described herein are generally configured to deliver a dose of the radioisotope therapy material to a human in need of treatment. As noted herein, the infusion method can avoid the use of "push" therapy which is commonly used to administer targeted radioisotope materials such as lutetium-177-DOTATATE. For example, in administration of many radioisotope therapy materials, the radioisotope therapy material is withdrawn from a vial into syringe. The syringe is then used to inject or "push" the radioisotope therapy material periodically into an IV line and into the patient over a 20-30 minute time span. Pushing of the materials through the syringe can result in inconsistent delivery of the materials to the patient and places the radioactive material in close proximity to the staff member injecting the material.

Figure 6:
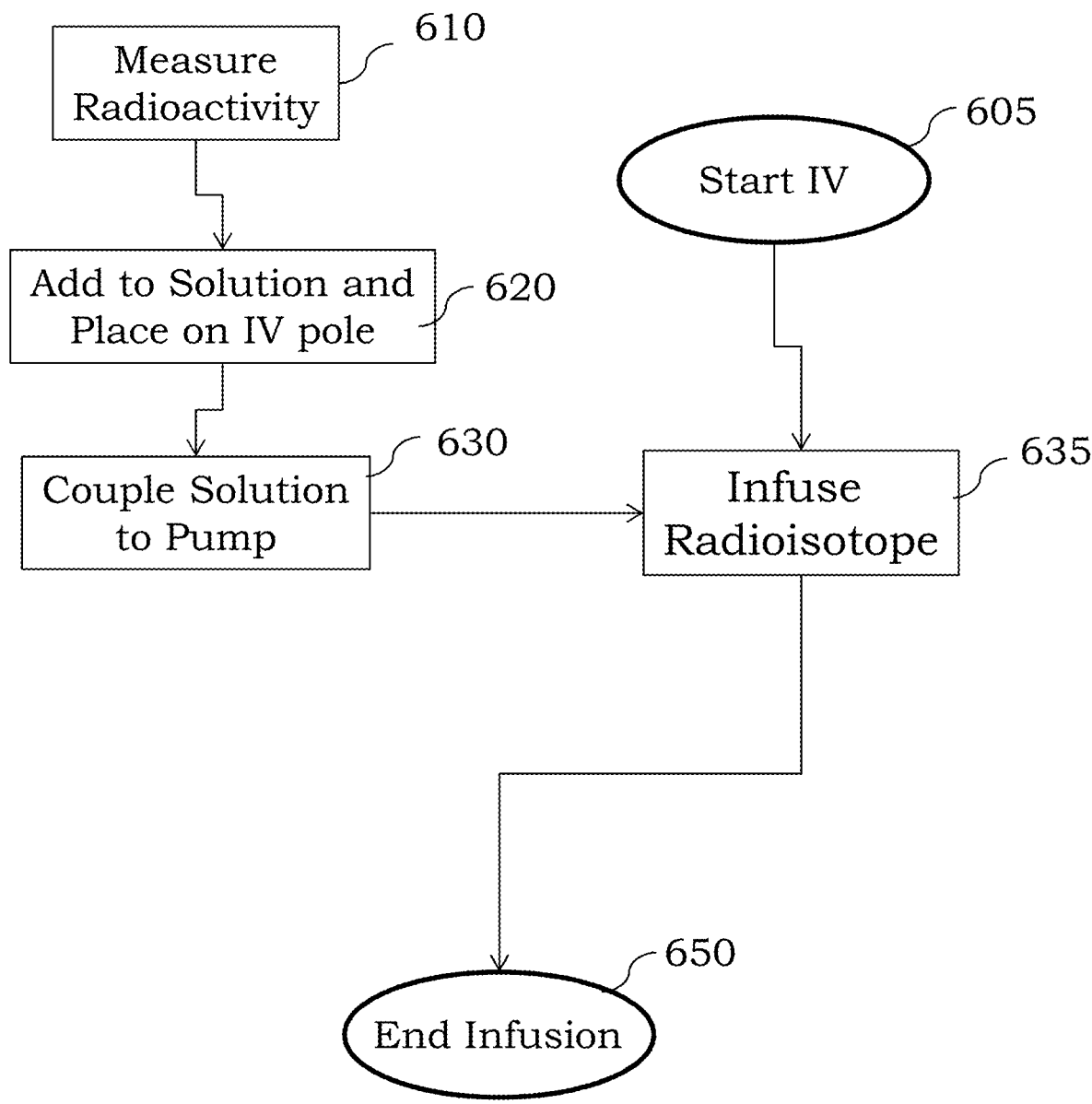
FIG. 6 is a flow chart showing certain process steps that can be used to administer a radioisotope therapy material to a human, in accordance with certain examples.

In certain embodiments, the infusion devices described herein can be used to deliver a radioisotope therapy material to a human in need of treatment in a more consistent and uniform manner. Illustrative disorders include cancer of neuroendocrine cells, bone cancer, B-cell lymphoma, non-Hodgkin's lymphoma, and other disorders. In general, the process involves infusing the radioisotope therapy material as it hangs within the infusion device on an IV pole. For example and referring to FIG. 6, a radioactivity level of the radioisotope material can be measured at step 610. A solution, e.g., saline or other materials, can then be used to dilute, suspend or otherwise provide a desired volume of the radioisotope therapy material, and the solution can be placed (or is already in) the infusion device, which is then placed on an IV pole at a step 620. A pump such as, for example, a peristaltic pump can then be fluidically coupled to the radioisotope therapy solution at step 630 to infuse the radioisotope material into the human at a step 635. The human typically already has an IV line or artery line (placed at step 605) that is introducing saline, dextrose, amino acids or other materials. The pump can introduce the radioisotope therapy material into this same IV or artery line without the need for human intervention during the infusion process. The radioisotope material can be delivered for a desired treatment period, e.g., 10 minutes to 120 minutes, at a desired flow rate, e.g., 1-10 mL/minute, until the infusion is ended at a step 650.

In certain embodiments, the infusion devices can be present in a kit optionally in combination with a radioisotope therapy material and written or electronic instructions. For example, the radioisotope therapy material can be lutetium-177-dotatate to treat a neuroendocrine tumor, and the kit further comprises written or electronic instructions for treatment of the human using the infusion device and the lutetium-177-dotatate. In other instances, the radioisotope material can be Lu-177-prostate-specific membrane antigen (PSMA) which can be used to treat prostate cancer. PSMA is a 750 amino acid type II transmembrane glycoprotein. See Rajasekaran A K et al., Am J Physiol Cell Physiol 2005; 288: C975-81. Radionuclides other than Lu-177 may also be present in the PSMA. In some examples, the targeted radionuclide therapy can be designed to bind to one or more of ER, PR and her2 receptors for treating breast cancer, neurotensin receptor for treating colorectal and pancreatic cancer, VEGF receptor for treating renal cell cancer or other receptors.

Certain specific examples are described of an infusion device and its use to treat a neuroendocrine tumor using lutetium-177-dotatate.

Example 1

Figure 7:
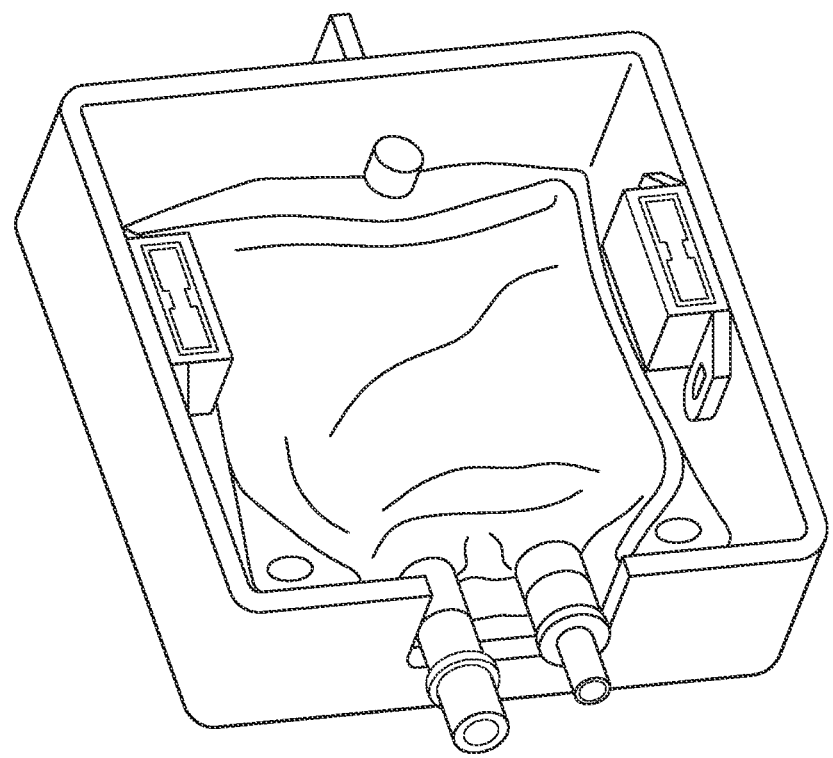
FIGS. 7 and 8 are photographs of one configuration of an infusion device that can be used to administer $^{177}$Lu-dotatate to a human in need of treatment for a neuroendocrine tumor, in accordance with some embodiments.
Figure 7:
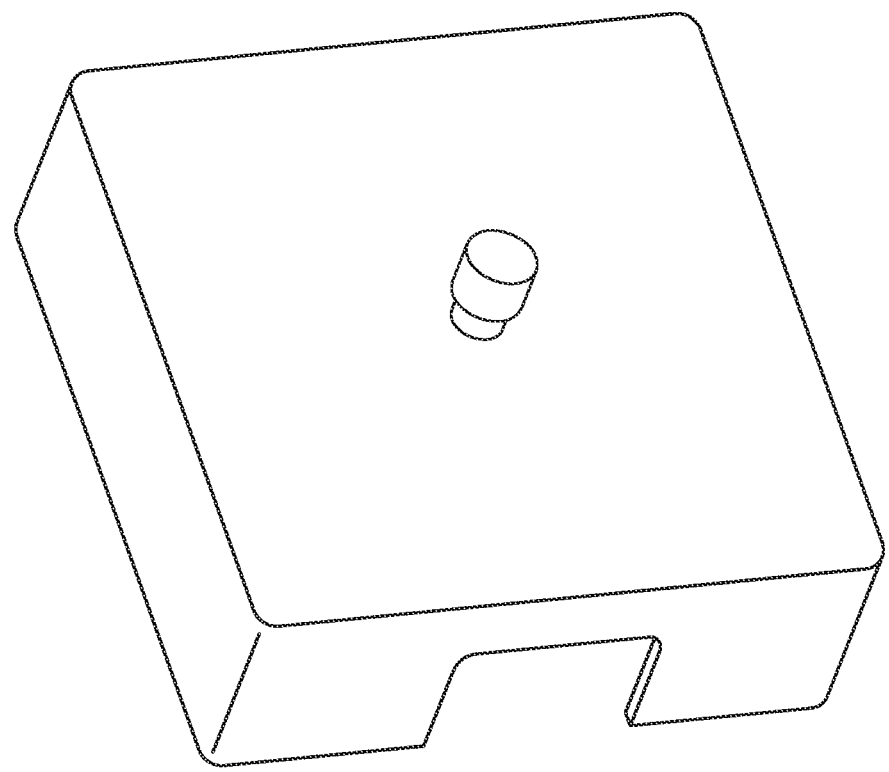
Figure 8:
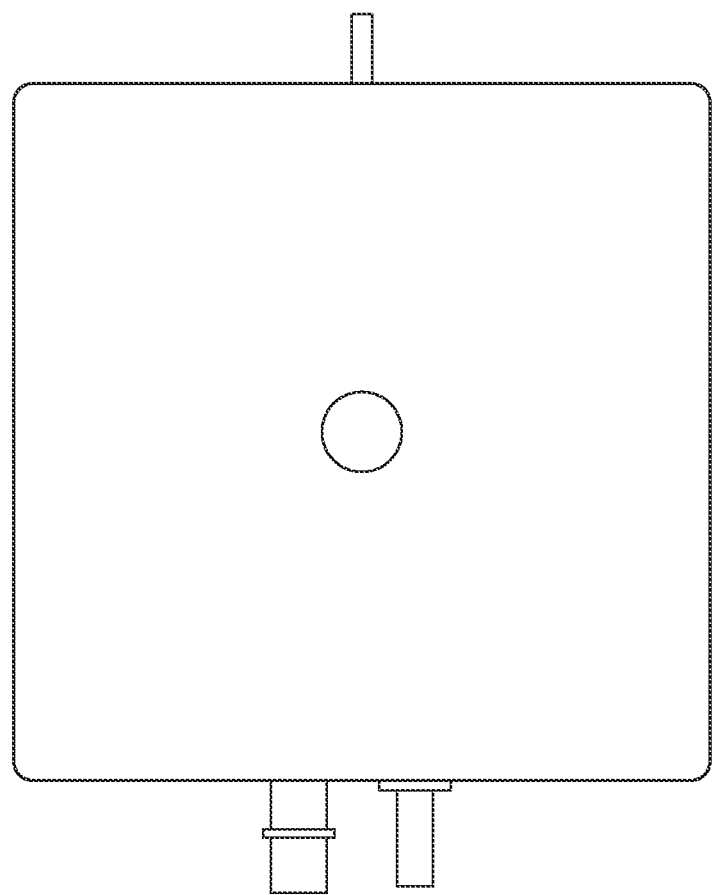
Figure 9:
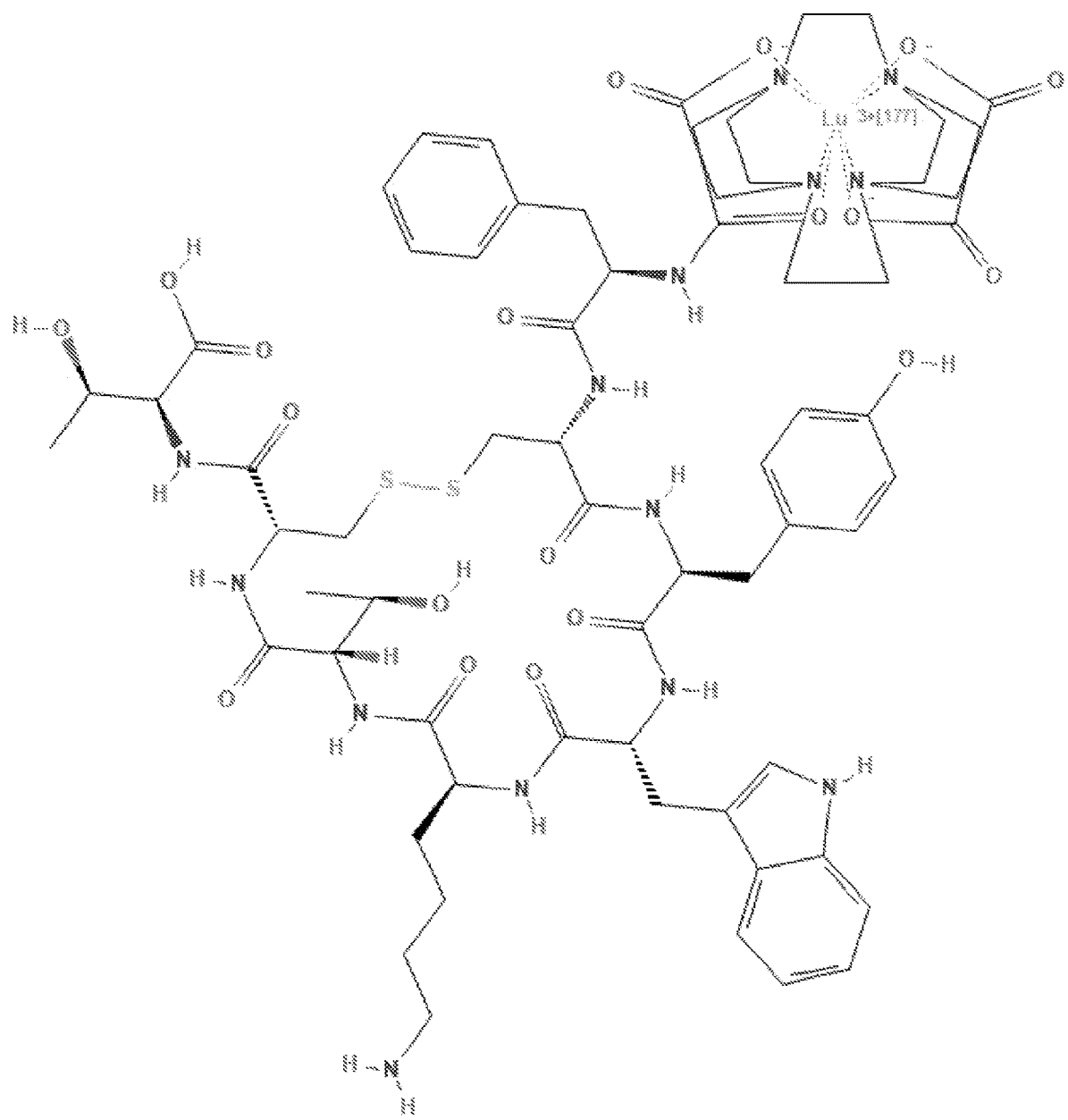
FIG. 9 shows the chemical structure for $^{177}$Lu-dotatate.

A photograph of an infusion device that can be used to administer lutetium-177-dotatate (chemical structure shown in FIG. 9) is shown in FIGS. 7 and 8. The infusion device is shown with the lid removed in FIG. 7 and shows an IV bag or container within the base. FIG. 8 shows the device with the lid coupled to the base and shows the fittings of the container penetrate through a port of the infusion device when the lid is attached. As noted below, one or both of these fittings can be used to couple the contents in the bag to a pump to infuse the lutetium-177-dotatate material into a human. The infusion device can be produced from acrylic, lead or other suitable materials that can provide an easy and appropriate material to stop beta radiation (or gamma radiation or both) and is stable enough to move into the prescribed work flow. An additional benefit of this device is it can lower radiation dose to staff members, because it allows them to be three feet further away from the radioactive patient.

While the exact process that can use the infusion device may vary, one illustration of an administration process is provided below. The following items were used to prepare a solution of the lutetium-177-dotatate for administration: 60 mL syringe, 1-18 g blunt needle, 19 g filter needle (vent needle), 18 g spinal needle (3.5 inches), 50 mL saline bag, Alcohol prep and a Small blue cap. A container containing the lutetium-177-dotatate was wiped using the alcohol wipe. The container was then opened and the dose was calibrated using a dose calibrator selected to measure Lu-177. Using the 50 mL saline bag, the 18 g needle was attached to the bag to remove 38 mL of saline. This step left about 20 mL of saline in the bag. 18 mL of the saline was ejected out of the 60 mL syringe (leaving about 20 mL in the syringe). The syringe was inverted a couple of times to coat the syringe with saline. The 19 g vent needle was then inserted into $^{177}$Lu Dotatate (LuDota) dose vial. The 18 g 3.5 inch spinal needle was then attached to the 60 mL syringe. All of the LuDota was removed (approximately 25 mL) from the container using the 60 mL syringe and spinal needle. Approximately 25 mL of LuDota was injected into the 50 mL saline bag resulting in about 65 mL total volume in the bag. The bag was then placed into a XL glove and placed in the dose calibrator. The bag was then placed into the infusion device shown in FIGS. 7 and 8 and delivered to the room where the patient was resident.

A primed IV line already coupled to the patient (typically used to administer saline and amino acids) was used to infuse the lutetium-177-dotatate solution. The primed line was coupled to an outlet of the bag in the infusion device, and the infusion device was placed on an IV pole near the patient. A pump was used to infuse the 65 mL of solution in the bag over a period of about 17 minutes.

When approximately 1 minute was left, the infusion device was lowered to permit about 65 mL of saline to backflow into the bag and refill it. The infusion device was then placed back above the patient and the solution was infused into the patient over a period of about 3 minutes. Once the bag was empty and the secondary line was empty, the bag was disconnected from the IV line. The treatment was complete. The patient was released when the radiation measurement from the umbilicus was less than 20 mrads per hour at 1 meter measurement distance.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. An infusion device configured to permit infusion of a radioisotope therapy material in an intravenous bag placed within the infusion device, the infusion device comprising:
a base; and
a lid configured to removably couple to the base, wherein each of the base and the lid is configured to absorb beta radiation emissions from the radioisotope therapy material and is configured to absorb gamma ray emissions from the radioisotope therapy material, and wherein the base and lid together are sized and arranged to receive the intravenous bag, wherein the base comprises a port to access a radioisotope therapy material introduced into the intravenous bag without removing the lid to permit infusion of the radioisotope therapy material in the intravenous bag to a human subject in need of treatment using the radioisotope therapy material, and wherein the port is configured to permit introduction of a fluid comprising the radioisotope therapy material into the intravenous bag to provide a desired level of the radioisotope therapy material to the human subject after emptying of the intravenous bag.

2. The infusion device of claim 1, wherein the lid removably couples to the base through a magnet in the base.

3. The infusion device of claim 1, wherein the lid removably couples to the base through hook and loop fastener.

4. The infusion device of claim 1, wherein the base comprises a first material comprising a polymeric material to absorb the beta radiation emissions and a second material comprising a metal to absorb the gamma ray emissions.

5. The infusion device of claim 4, wherein the polymeric material comprises an acrylic and the metal comprises one or more of lead, antimony, bismuth, and tin.

6. The infusion device of claim 4, wherein the metal is present as metal nanoparticles.

7. The infusion device of claim 1, further comprising an electronic device in the base or the lid or both.

8. The infusion device of claim 7, wherein the electronic device comprises an internal radiation sensor.

9. The infusion device of claim 7, wherein the electronic device comprises a processor.

10. The infusion device of claim 1, wherein the port is configured to permit backflow of fluid into the intravenous bag during treatment and deliver the entire contents of the intravenous bag to the human subject during treatment to empty the intravenous bag.

11. An infusion device comprising:
an enclosure comprising an intravenous bag; and
a radioisotope therapy material in the intravenous bag, wherein the enclosure comprises a port to access the radioisotope therapy material in the intravenous bag, wherein the enclosure is configured to absorb beta radiation emissions from the radioisotope therapy material and to absorb gamma ray emissions from the radioisotope therapy material, and wherein the port is configured to permit introduction of a fluid into the intravenous bag to provide a desired level of the radioisotope therapy material after emptying of the intravenous bag.

12. The infusion device of claim 11, wherein the enclosure further comprises a lid removably coupled to a base.

13. The infusion device of claim 12, wherein the lid removably couples to the base through hook and loop fastener or through a magnet.

14. The infusion device of claim 11, wherein the enclosure comprises a first material comprising a polymeric material to absorb the beta radiation emissions and a second material comprising a metal to absorb the gamma ray emissions.

15. The infusion device of claim 14, wherein the polymeric material comprises an acrylic and the metal comprises one or more of lead, antimony, bismuth, and tin.

16. The infusion device of claim 14, wherein the metal is present as metal nanoparticles.

17. The infusion device of claim 11, further comprising an electronic device in the enclosure.

18. The infusion device of claim 17, wherein the electronic device comprises an internal radiation sensor.

19. The infusion device of claim 17, wherein the electronic device comprises a processor.

20. The infusion device of claim 11, wherein the port is configured to permit backflow of fluid into the intravenous bag during treatment and deliver the entire contents of the intravenous bag to empty the intravenous bag.

21. An infusion device comprising:
an enclosure; and
a radioisotope therapy material in the enclosure, wherein the enclosure comprises a port to access the radioisotope therapy material in the enclosure, and wherein the enclosure is configured to absorb beta radiation emissions from the radioisotope therapy material and to absorb gamma ray emissions from the radioisotope therapy material, wherein the radioisotope therapy material is present in a container that is permanently coupled to the enclosure.

* * * * *